United States Patent [19]

Kesting

[11] 4,280,970

[45] Jul. 28, 1981

[54] POLYOXYETHYLENE GRAFTED MEMBRANE MATERIALS WITH GRAFTING LINKS DERIVED FROM A DIISOCYANATE

[75] Inventor: Robert E. Kesting, Irvine, Calif.

[73] Assignee: Puropore Inc., Tustin, Calif.

[21] Appl. No.: 4,828

[22] Filed: Jan. 19, 1979

[51] Int. Cl.³ .................. B01D 39/16; B01D 39/18; B29D 11/00; G02C 7/04
[52] U.S. Cl. .................. 264/1.7; 210/650; 210/654; 210/500.1; 210/500.2; 260/9; 260/13; 264/215; 264/216; 264/217; 264/218; 351/160 H; 427/385.5; 428/412; 428/526; 428/534; 525/424
[58] Field of Search ............. 8/192, 187; 210/23 F, 210/23 H, 500 R, 500 M; 260/9, 13; 264/1, 171, 215, 216, 217, 218; 351/160 H; 427/385 R; 428/412, 526, 534; 525/424

[56] References Cited

U.S. PATENT DOCUMENTS

| | | | |
|---|---|---|---|
| 3,112,984 | 12/1963 | Aldridge | 8/192 |
| 3,723,377 | 3/1973 | Spangler | 8/187 |
| 3,738,981 | 6/1973 | Graff et al. | 8/192 |
| 3,786,034 | 1/1974 | Blair et al. | 264/1 |
| 3,810,956 | 5/1974 | Kimura et al. | 525/424 |
| 3,821,136 | 6/1974 | Hudgin et al. | 351/160 H |
| 3,822,238 | 7/1974 | Blair et al. | 351/160 H |
| 4,089,649 | 5/1978 | Mares et al. | 8/192 |
| 4,092,286 | 5/1978 | Noll et al. | 8/192 |

*Primary Examiner*—J. C. Cannon
*Attorney, Agent, or Firm*—Knobbe, Martens, Olson, Hubbard & Bear

[57] ABSTRACT

Membrane forming polymers are converted to hydrophilic polymeric membranes by (a) grafting a polyoxyethylene chain to a membrane forming polymer structure and thereafter forming a membrane; (b) coating a membrane with a polymer to which a polyoxyethylene chain has been grafted; or (c) grafting in situ a polyoxyethylene chain to a formed membrane polymer.

37 Claims, No Drawings

POLYOXYETHYLENE GRAFTED MEMBRANE MATERIALS WITH GRAFTING LINKS DERIVED FROM A DIISOCYANATE

TECHNICAL FIELD

This invention relates to membranes and films useful for dialysis, microfiltration, ultrafiltration, reverse osmosis, and other membrane and film applications, contact lens blanks, and to methods of polymer preparation to form such products. More specifically, this invention relates to methods of forming hydrophilic membranes and polymer structures.

BACKGROUND OF THE INVENTION

Kesting (1–10, 12) and Kesting et al (11, 13–16), incorporated herein by reference, have described many types of membranes and methods of preparation of the same. Kesting (1), Chapter 3, describes dense membranes and Kesting (1), Chapter 5, describes porous phase-inversion membranes. Applications of membranes, generally, are described by Kesting (1), Chapter 9. Kesting has also described cellulose acetate membranes and methods of forming the same (4). Modified cellulosic membranes (7, 18) and specially configured cellulosic membranes (8, 17) have also been described by Kesting et al. The literature on cellulose, cellulose derivatives, and the reactions of cellulose is extremely voluminous. See. e.g., Ott et al, Eds., "Cellulose and Cellulose Derivatives", *High Polymers,* Vol. V, especially Section IX (Interscience, 1954) and Kirk-Othmer *Encyclopedia of Chemical Technology,* Vol. 4, Pages 593–683 (2nd edn., 1967), and the numerous references cited therein. Further background as to membranes, membrane materials and membrane forming methods is found in the voluminous patent literature (See, e.g., references 19–47) and in the general technical literature on this subject.

The chemistry of isocyanates is well-known, see, e.g., Kirk-Othmer *Encyclopedia of Chemical Technology,* 2 MD Edn, Vol. 12, Pages 45–64, and the numerous references cited therein.

Generally speaking, the technology for preparation of cellulose esters in which most, but not all, hydroxyl groups on the cellulosic molecule are esterified with, most commonly, acetate or nitrate substituents and, less commonly, with other substituents, e.g., propionate and butyrate substituents, is very well known. It is also recognized that the residual hydroxyl groups on the cellulose molecule are subject to reaction with the same or different substituent groups. The reaction of isocyanates with alcohols and other compounds which include a reactive hydroxyl group is an extremeely well known reaction. It is also known that the reaction of phenols and isocyanates, and other blocking or capping agents and isocyanates, is reversible at temperatures ranging from about 100° C. to 150° C. and higher. Blocked isocyanates, sometimes called "splitters", are commercially used to generate free isocyanates in situ. For example, blocked isocyanates are used in systems in which a film is formed and cured, or cross-linked by subsequent heating, e.g., baked coating or enamel.

Cellulose acetate membranes are among the oldest and most well known of all the membrane systems, and, in spite of serious limitations, remain among the most important membranes technically and commercially. Alternative polymeric systems have been explored in efforts to overcome the disadvantages of cellulose based membrane systems. Cellulose acetate carbamates are old and have been described by Malm and Nadeau in U.S. Pat. No. 1,991,107, February 12, 1935, by Hearon, Hiatt and Fordyce, J. Am. Chem. Soc., 65, 829, 833 (1943) and by Hearon and Lobsitz, J. Am. Chem. Soc., 70, 296 (1948). Phenylisocyanate, phenylisothiocyanate and allylisothiocyanate, are mentioned in the preparation of cellulose acetate derivatives. Membranes from isocyanates and isothiocyanates are not mentioned, however.

The chemistry of polyethylene glycols and polyoxyethylene surfactants is also very well developed. See, e.g., Kirk-Othmer *Encyclopedia of Chemical Technology,* Vol. 19, Pages 531–548; McCutcheon's DETERGENTS AND EMULSIFIERS, Allured Publishing Corporation, Ridgewood, N.J. 07450.

In general, the chemistry of detergents which are suitable for being grafted onto polymers and the membranes according to the principles of this invention is well known. See generally, Kirk-Othmer *Encyclopedia of Chemical Technology,* Vol. 19, Pages 507–593; McCutcheon's DETERGENTS AND EMULSIFIERS, supra.

Nearly all of the polymers suitable for use in membranes, i.e., membrane forming polymers, and many polymers suitable for use in films, contact lenses and the like, tend to be hydrophobic and, typically, are treated with a surface active coating before or in conjunction with use to provide a wettable polymeric structure. The use of an added surface active agent is satisfactory in many applications but frequently is unsatisfactory or detrimental because the surfaceactive material is subject to being leached from the polymer, providing a source of contamination or reducing the effectiveness of the polymer structure, or both. It is a principle feature of this invention to provide polymer systems which include non-leachable surface active graft copolymers.

BRIEF SUMMARY OF THE INVENTION

This invention comprises methods forming hydrophilic membranes and other structures, and the resulting membranes and other polymeric products, e.g., films and lens blanks. The methods involve the addition to membranes, or other structures, of polyoxyethylene polymer substituents by graft either before or after membrane formation or by treating membranes or other structures with polyoxyethylene substituent graft copolymer after formation. Specifically, the methods include: (a) grafting a polyoxyethylene polymer to a membrane forming polymer by reaction of the membrane forming polymer and the polyoxyethylene polymer with a diisocyanate (or equivalent grafting link reagent) and then forming a membrane, or other structure of the resulting graft copolymer; (b) attaching a diisocyanate (or equivalent grafting link) to a membrane forming polymer or polyoxyethylene polymer, casting the thus modified polymer in mixture with an unmodified polyoxyethylene or membrane forming polymer to form a membrane, or other structure, and thereafter causing the grafting link reagent to graft the polyoxyethylene polymer to the membrane; or (c) grafting a polyoxyethylene polymer to a membrane forming polymer and thereafter coating a membrane, or other structure, with the resulting graft copolymer. The invention includes membranes, and other structures, thus prepared.

DETAILED DESCRIPTION OF THE INVENTION

The polymer systems of this invention are formed from (a) membrane, film and the lens forming membranes, (b) polyoxyethylene polymers, e.g., polyethylene glycol and blocked polyoxyethylenes, and (c) polymer substituents to provide active sites for grafting polyoxyethylene polymers to the membrane forming polymer, film forming polymer or lens polymer, i.e., a grafting link reagent.

Currently available, microfiltration membranes are made from essentially hydrophobic polymers such as cellulose nitrate, cellulose acetate, blends of cellulose nitrate and cellulose acetate, cellulose triacetate, polycarbonate, and polysulfone, as well as other polymers. Membranes of these materials, once formed, are usually rendered hydrophilic by the inclusion of surfactant in the casting solution or by a post membrane formation treatment consisting of immersing the material in an aqueous solution of the surfactant. In both cases, although wettability is imparted, the membranes typically contain between 2 and 6% of water extractable (leachable) materials which are potential contaminants of any filtrate. These potential contaminants are eliminated according to the present invention by covalent attachment of surface active substituents to the polymer prior to membrane formation, or in situ within the already formed membrane, or by post-formation treatment of membranes by graft copolymer.

Premodification of Polymer

According to one facet of the present invention, a polymer is modified before being cast or formed into the end physical configuration. For example, hydrophilic membranes, films, or lens blanks may be formed from a polymer which has been modified before being cast into the membrane, film or lens blank, or other, configuration to include as an integral part of the polymer a surface active polyoxyethylene substituent.

For example, tolylene diisocyanate is reacted with an equimolar portion of nonylphenoxypoly(ethyleneoxy)ethanol (IGEPAL, (trademark) CO-990, GAF Corporation). The resulting diisocyanate compound, one end reacted with the surface active polyoxyethylene compound and the other end free isocyanate, is dissolved in a dioxolane solution containing cellulose acetate. In a particular example, 250 gms. of tolylene diisocyanate-polyoxyethylene, reacted as above, was added to 2 l. of dioxolane solution containing 125 grams of cellulose acetate and allowed to react for three days at 50° C. before precipitation, washing and drying. Solutions of this polymer were then made, cast and dried. The resultant films were useful in dialysis applications. Neither the time nor temperature are critical and time and temperature are reciprocally related. At room temperature, the free end of the diisocyanate grafting compound will react with cellulose acetate to bond the polyoxyethylene polymer to the cellulose acetate; however, the reaction proceeds more rapidly at higher temperatures. Any temperature which does not decompose or degrade the polymers may be used.

In addition the diisocyanate may be blocked at the free end with a thermally active block, e.g., 2-ethylimidazole, to form a splitter compound which, upon being heated, frees the diisocyanate to react with the cellulose acetate.

While it is preferred to use an unblocked diisocyanate in some applications, blocked diisocyanates may be used where the blocking substituent is not objectionable or can be reasonably removed.

Reacting 100 grams of a comparable reaction product of hexamethylene diisocyanate with 2-ethylimidazole and nonylphenoxypoly(ethylenoxy)ethanol with 250 grams of cellulose acetate or cellulose nitrate produces polymers which are wettable and contain no water leachable surfactants.

Similarly, the blocked hexamethylene diisocyanatenonylphenoxypoly(ethyleneoxy)ethanol reaction product is reacted with cellulose acetate-butyrate, to form a polymer which is then cast as hydrophilic contact lens blanks. These blanks, when annealed, and formed, yield wettable cellulose acetate-butyrate contact lenses.

In Situ Formation

One mole of polyethylene glycol, molecular weight 4000, (CARBOWAX (trademark) 4000, Union Carbide) was reacted with two moles of tolylene diisocyanate, thus forming a polyoxyethylene polymer which terminated at each end with an active isocyanate group. The polyoxyethylene-di(tolylene diisocyanate) thus formed was dissolved in propylene oxide and the resulting solution was added to a propylene oxide solution of cellulose acetate to form a casting solution. The casting solution was stirred and cast as soon as entrapped bubbles had risen to the surface. (The solution must be cast soon after formation because the solution gels on standing.) A clear, dense film was formed and heated to 150° C. for ½ hour. The film was a hydrophilic, cross-linked cellulose acetatepolyoxyethylene film suitable for dialysis.

In an alternative procedure, one mole of polyoxyethylene-di(tolylene diisocyanate), formed as above, was reacted with 2 moles of 2-ethylimidazole before mixing with the cellulose acetate solution. The resultant solution was stable and could be stored for an extended period before casting. Annealing the film at 60° C. for 24 hours effected the splitting off of the 2-ethylimidazole and the formation of the cross-linked graft copolymer of cellulose acetate-polyoxyethylene which was suitable for dialysis after washing to remove the imidazole.

Post-Formation Coating of Hydrophobic Membranes

In another embodiment of the invention, membranes, films, lenses or other physical forms of polymeric structures, are surface treated with block copolymer containing non-leachable covalently bonded polyoxyethylene. For example, a membrane, film or lens of an already formed hydrophobic polymer is coated with an organic solution of a water-insoluble surface active polyoxyethylene block copolymer, the solvent being so selected that the polymeric material is inert to the organic solvent employed for the surface active copolymer constituent. For example, the cellulose acetate graft of nonylphenoxypoly(ethyleneoxy)ethanol, previously described, in trifluorethanol as the solvent, was used to coat a cellulose nitrate microporous membrane. After drying, the membrane was water-wettable and extraction with hot or cold water yielded zero leachables. Similarly, a polycarbonate membrane (Reference 5) was immersed in a 1% solution of the aforementioned cellulose acetate-polyoxyethylene graft polymer in trifluorethanol solvent. After drying, the membrane was water-wettable with zero leachables by hot or cold water. Other solvents may be used, of course, provided they do not dissolve or adversely effect the characteristics of the membrane, film or polymer substrate. For example, while methylene chloride is a satisfactory solution for the cellulose-acetate polyoxyethylene polymer in treating cellulose nitrate membranes, it is not a suitable solvent for use in treating polycarbonate membranes because of the solubility of polycarbonate in the solvent.

In another example, the grafted cellulose acetate-polyoxyethylene polymer is used as an assisting polymer in a polymer assisted phase inversion process (Reference 6). Thus, a cellulose acetate-polyoxyethylene graft copolymer in trifluorethanol is added to nylon 66 in trifluorethanol and the resulting solution is cast into a film. After drying, the film is leached with a suitable solvent to remove excess cellulose acetate-polyoxyethylene graft polymer, with a non-solvent for the nylon 66, e.g., dioxolane, thus producing a wettable, microporous nylon 66 membrane.

For membrane applications, a preferred polymer system useful in this invention is cellulose acetate. Cellulose acetate is by far the most widely used polymer system and, presently, finds wide applicability in the present invention. Other cellulose esters may, however, be used. For example, cellulose acetate-propionate, cellulose acetate-butyrate, cellulose nitrate, and other cellulose esters may also be used in this process. In addition, the cellulosic polymers useful in this invention may include cellulose ethers and other mono- or di-substituted cellulose polymer systems. The essential requirement of cellulose polymers useful in this invention is that there be available on the cellulose polymer structure reactive hydroxyl groups. For present purposes, cellulose acetate is selected as exemplary of the cellulosic polymers useful in this invention and as the most preferred polymer for most applications.

Cellulosic acetate specifically, and cellulose esters and other cellulosic polymers generally, may have a degree of substitution of up to about 2.8. Preferably, the D.S. equal 2.3–2.5 and cellulose polymers with a D.S. of 2.0 to 2.8 are generally very suitable. Polymers with a lower degree of substitution may also be used; however, polymers with a degree of substitution much above 2.8 lack a sufficient number of reactive hydroxyl groups to permit major modification of the basic cellulose polymer structure characteristics by the present invention.

Generally speaking, any partially substituted cellulose ester or comparable cellulose derivative which is sufficiently soluble in a casting solution which is also a solvent for the isocyanate constituent of the solution may be used in this invention. The foregoing criteria are given as general guidelines and not as limiting the class of polymers suitable for use in this invention. Cellulose acetate, as the most highly preferred polymer system, and cellulose nitrate as another highly preferred system are mentioned as exemplary only.

In addition to the preferred cellulosic polymers which are preferred for many applications and which exemplify (but do not limit) the invention, noncellulosics, such as nylon 66 for example, which contain active hydrogens capable of reaction with isocyanates are also suitable polymeric systems suitable for reaction, through isocyanate, or other grafting compounds, with polyoxyethylene containing polymers to form hydrophilic polymer products.

Solvents for cellulose acetate, or cellulose nitrate, or the cellulose polymer which constitutes the polymeric constituent of the casting solution, are suitable for use in this invention. Generally speaking, no special modifications of the solvent system are required for carrying out this invention, since the isocyanates, generally, will be soluble in the solvent systems suitable for cellulosic polymers. In any event, suitable solvent systems can be readily ascertained from standard tables of solubility of the respective polymeric and isocyanate constituents. Typical of the solvent systems useful in this invention are acetone and dioxolane, alone or blended. Kesting (1) includes a discussion of solvents and solvent effects and criteria for solvent selection and Kesting et al (2–18) include numerous examples of suitable solvents.

Soluble diisocyanates generally are suitable for use in this invention. Hexamethylene diisocyanate and tolylene diisocyanate are most suitable candidates for use in this invention. Oximes generally, e.g., acetone oxime, methyl ethyl ketone oxime, cyclohexanone oxime, benzyldehyde oxime, 2-pentenone oxime, may be used as blocking agents. Additional preferred blocking agents include 2-alkylimidazoles such as 2-methylimidazole, 2-ethylimidazole, 2-propylimidazole, and 2-isopropylimidazole.

Polyoxyethylenes suitable for use in this invention include polyoxyethylene per se, i.e., polyethylene oxide, single end blocked polyethylene glycols and hydrophilic copolymers of polyethylene glycols such as polypropylene oxide-polyethylene oxide block copolymers. Nonylphenoxypoly(ethyleneoxide)ethanol is a preferred single end blocked polyoxyethylene, but analogous octylphenoxy- blocked polymers are also quite satisfactory. In general, any polyoxyethylene surfactant which includes a reactive hydroxyl group, see McCutcheon's DETERGENTS AND EMULSIFIERS, is a suitable candidate for this invention. Crosslinked polymers, wherein the cross-linking polymer is the polyoxyethylene requires, of course, di-hydroxy functional polyoxyethylene polymers. All of the above-mentioned polyoxyethylenes are, generically, encompassed in the term "polyoxyethylene" as used herein.

Industrial Applicability

Membranes formed according to the principles of this invention find wide industrial applicability. For example, these membranes are excellent microfiltration media and are suitable, depending upon the exact mode of formation and polymeric composition, for use in ultrafiltration, reverse osmosis, and electrophoresis. Films are excellent dialysis membranes and are suitable for use in analytical electrodes as semipermeable membranes, and more generally are useful as coatings. Lens blanks are suitable for forming optical contact lenses.

The foregoing examples and applications describe the best mode of the invention as presently contemplated but are exemplary of the invention and not limiting as to the application or the scope of the principles of the invention.

References

The following references are incorporated in the foregoing discussion as background prior art as fully as if fully repeated therein:
1. Kesting, R. E., Synthetic Polymeric Membranes, McGraw-Hill, 1971,
2. U.S. Pat. No. 3,290,286, Kesting, Dec. 6, 1966.
3. U.S. Pat. No. 3,332,894, Cantor & Kesting, July 25, 1967.
4. U.S. Pat. No. 3,884,801, Kesting, May 20, 1975.

5. U.S. Pat. No. 3,945,926, Kesting, Mar. 23, 1976.
6. U.S. Pat. No. 3,957,651, Kesting, May 18, 1976.
7. U.S. Pat. No. 4,035,457, Kesting, July 12, 1977.
8. U.S. Pat. No. 4,035,459, Kesting, July 12, 1977.
9. U.S. Pat. No. 4,048,271, Kesting, Sept. 13, 1977.
10. R. Kesting, "The Role of the Membrane Salt in Cellulose Casting Solution," paper presented at the ACS meeting in Los Angeles, April, 1963.
11. R. Kesting and A. Menefee, "The Role of Formamide in the Preparation of Cellulose Acetate Membranes by the Phase Inversion Process," Kolloid Z u Z. Polymere, 232, 341 (1969).
12. R. Kesting, "Cellulose Acetate Membranes for Deslaination in the Process of Reverse Osmosis, I Lytropic Swelling of Secondary Cellulose Acetate," J. Appl. Polymer Sci., 9, 663 (1965).
13. R. Kesting, M. Barsh and A. Vincent, "Cellulose Acetate ... II Parameters Affecting Membrane Gel Structure," J. Appl. Polymer Sci., 9, 1873 (1965).
14. A. Vincent, M. Barsh and R. Kesting, "Cellulose Acetate ... III Bound Water Relationships," J. Appl. Polymer Sci., 9, 2363 (1965).
15. OSW R&D Reports 117 and 154.
16. R. E. Kesting, K. F. Jackson and J. M. Newman, "DRY-RO ® Membranes of Quaternized Cellulose Triesters for the Single Pass Demineralization of Sew Water in Reverse Osmosis," presented at the Fifth International Symposium on Fresh Water from the Sea in Sardinia, May, 1976.
17. R. Kesting, "Asymmetric Cellulose Acetate Membranes," Chapter 5 in Reverse Osmosis and Synthetic Membranes, S. Sourirajan, ed., National Research Council of Canada.
18. Kesting, R. E., Jackson, K. F. and Newman, J. M., "Dry-RO ® Membranes of the Anionic Cellulose Triesters for Desalination in the Process of Reverse Osmosis," Proc. 6th Intern Symposium, Fresh Water from the Sea, Vol. 3, 213-217 (1978).
19. U.S. Pat. No. 3,228,876, Mahon, Jan. 11, 1966.
20. U.S. Pat. No. 3,288,877, Mahon, Jan. 11, 1966.
21. U.S. Pat. No. 3,373,056, Martin, Mar. 12, 1968.
22. U.S. Pat. No. 3,422,008, McLain, Jan. 14, 1969.
23. U.S. Pat. No. 3,423,491, McLain et al, Jan. 21, 1969.
24. U.S. Pat. No. 3,450,650, Murata, June 17, 1969.
25. U.S. Pat. No. 3,445,460, Mahon et al, July 15, 1969.
26. U.S. Pat. No. 3,475,331, McLain, Oct. 28, 1969.
27. U.S. Pat. No. 3,585,126, Cannon, June 15, 1971.
28. U.S. Pat. No. 3,615,024, Michaels, Oct. 26, 1971.
29. U.S. Pat. No. 3,653,180, Juliano et al, Apr. 4, 1972.
30. U.S. Pat. No. 3,654,065, Doragi, Apr. 4, 1972.
31. U.S. Pat. No. 3,655,591, Seiner, Apr. 11, 1972.
32. U.S. Pat. No. 3,674,628, Fabre, July 4, 1972.
33. U.S. Pat. No. 3,674,719, Jenkins, July 4, 1972.
34. U.S. Pat. No. 3,724,672, Leonard et al, Apr. 3, 1973.
35. U.S. Pat. No. 3,520,960, Douglas, July 21, 1970.
36. U.S. Pat. No. 3,755,034, Mahon et al, Aug. 28, 1973.
37. U.S. Pat. No. 3,762,136, Kimura, Oct. 2, 1973.
38. U.S. Pat. No. 3,780,147, Stana, Dec. 18, 1973.
39. U.S. Pat. No. 3,781,378, Kantor et al, Dec. 25, 1973.
40. U.S. Pat. No. 3,792,135, Brown et al, Feb. 12, 1974.
41. U.S. Pat. No. 3,798,185, Skiens et al, Mar. 19, 1974.
42. U.S. Pat. No. 3,799,365, Salger et al, Mar. 26, 1974.
43. U.S. Pat. No. 3,806,564, Riley et al, Apr. 23, 1974.
44. U.S. Pat. No. 3,852,224, Bridgeford, Dec. 3, 1974.
45. U.S. Pat. No. 3,852,388, Kimura, Dec. 3, 1974.
46. U.S. Pat. No. 3,930,105, Christen, Dec. 30, 1975.
47. U.S. Pat. No. 3,933,653, Hashino et al, Jan. 20, 1976.
48. Brandrupt, J. and Immergut, E. H., Polymer Handbook, Interscience (1966).
49. Billmeyer, F. W., Textbook of Polymer Science, 2nd Ed., Wiley-Interscience, 1971.

I claim as my invention:

1. A hydrophilic membrane consisting essentially of the graft copolymer of an active hydrogen containing membrane forming polymer, a diisocyanate grafting link and an active hydrogen containing polyoxyethylene polymer.

2. The membrane of claim 1 wherein the membrane forming copolymer is a cellulosic polymer or nylon.

3. A hydrophilic membrane comprising a hydrophobic polymer coated with a hydrophilic graft copolymer of a polyoxyethylene polymer, a diisocyanate grafting link and an active hydrogen containing membrane forming polymer.

4. A hydrophilic film consisting essentially of the graft copolymer of an active hydrogen containing film forming polymer a diisocyanate grafting link and an active hydrogen containing polyoxyethylene polymer.

5. The film of claim 4 wherein the film forming copolymer is a cellulosic polymer or nylon.

6. A hydrophilic film comprising a hydrophobic polymer coated with a hydrophilic graft copolymer of a polyoxyethylene polymer a diisocyanate grafting link and an active hydrogen containing film forming polymer.

7. A contact lens consisting essentially of a graft copolymer of polyoxyethylene polymer, a diisocyanate grafting link, and a cellulose acetate-butyrate polymer.

8. The method of forming a membrane comprising the steps of grafting an active hydrogen containing polyoxyethylene polymer to an active hydrogen containing membrane forming polymer through a diisocyanate grafting link to produce a graft copolymer, forming a casting solution of the graft copolymer, and casting a membrane of said graft copolymer by a phase inversion process.

9. The method of claim 8 wherein the membrane forming polymer is a cellulosic polymer.

10. The method of claim 8 wherein the membrane forming polymer is nylon.

11. The method of forming a film comprising the steps of grafting an active hydrogen containing polyoxyethylene polymer to an active hydrogen containing film forming polymer through a diisocyanate grafting link to produce a graft copolymer, forming a casting solution of the graft copolymer, and casting a film of said graft copolymer by a phase inversion process.

12. The method of claim 11 wherein the film forming polymer is a cellulosic polymer.

13. The method of claim 11 wherein the film forming polymer is nylon.

14. The method of forming a membrane comprising the steps of forming a casting solution containing a reactive hydrogen containing membrane forming polymer, a reactive hydrogen containing polyoxyethylene polymer, and a soluble diisocyanate; casting a membrane of said casting solution; and thereafter holding the resulting membrane at a temperature between ambient room temperature and the degradation temperature of the membrane forming polymer to cause the diisocyanate to graft the polyoxyethylene polymer to the membrane forming polymer.

15. The method of claim 14 wherein the membrane forming polymer is a cellulosic or nylon membrane forming membrane.

16. The method of claim 14 wherein the diisocyanate is reacted with either the membrane forming polymer or the polyoxyethylene polymer before the casting solution is formed.

17. The method of claim 16 wherein the diisocyanate is reacted with the polyoxyethylene polymer before the casting solution is formed.

18. The method of claim 17 wherein the membrane forming polymer is a cellulosic or nylon membrane forming membrane.

19. The method of claim 17 wherein the cast membrane is held at a temperature of from 50° C. to 150° C. to cause reaction of diisocyanate polyoxyethylene polymer with the membrane forming polymer.

20. The method of claim 19 wherein the membrane forming polymer is a cellulosic or nylon membrane forming membrane.

21. The method of claim 17 wherein the polyoxyethylene polymer has two reactive hydrogens, each of which is reacted with a diisocyanate, thereby forming a cross-linking agent for the membrane forming polymer.

22. The method of claim 18 wherein the cast membrane is held at a temperature of from 50° C. to 150° C. to cause reaction of diisocyanate polyoxyethylene polymer with the membrane forming polymer.

23. The method of claim 22 wherein the membrane forming polymer is a cellulosic or nylon membrane forming polymer.

24. The method of forming a film comprising the steps of forming a casting solution containing a reactive hydrogen containing film forming polymer, a reactive hydrogen containing polyoxyethylene polymer, and a soluble diisocyanate; casting a film of said casting solution; and thereafter holding the resulting film at a temperature between ambient room temperature and the degradation temperature of the film forming polymer to cause the diisocyanate to graft the polyoxyethylene polymer to the film forming polymer.

25. The method of claim 24 wherein the film forming polymer is a cellulosic or nylon film forming film.

26. The method of claim 24 wherein the diisocyanate is reacted with either the film forming polymer or the polyoxyethylene polymer before the casting solution is formed.

27. The method of claim 26 wherein the diisocyanate is reacted with the polyoxyethylene polymer before the casting solution is formed.

28. The method of claim 27 wherein the film forming polymer is a cellulosic or nylon film forming film.

29. The method of claim 27 wherein the cast film is held at a temperature of from 50° C. to 150° C. to cause reaction of diisocyanate polyoxyethylene polymer with the film forming polymer.

30. The method of claim 29 wherein the film forming polymer is a cellulosic or nylon film forming film.

31. The method of claim 27 wherein the polyoxyethylene polymer has two reactive hydrogens, each of which is reacted with a diisocyanate, thereby forming a cross-linking agent for the film forming polymer.

32. The method of claim 28 wherein the cast film is held at a temperature of from 50° C. to 150° C. to cause reaction of diisocyanate polyoxyethylene polymer with the film forming polymer.

33. The method of claim 32 wherein the film forming polymer is a cellulosic or nylon film forming polymer.

34. The method of producing a hydrophilic membrane comprising coating a hydrophobic membrane with a graft copolymer of a membrane forming, active hydrogen containing polymer to which has been grafted through a diisocyanate grafting link an active hydrogen containing polyoxyethylene polymer; the graft copolymer being soluble in a non-solvent for the hydrophobic membrane polymer.

35. The method of forming a hydrophilic contact lens blank comprising grafting polyoxyethylene polymer to cellulosic lens forming polymer and forming a contact lens blank from said grafted polymer.

36. The method of claim 35 wherein the lens forming polymer is cellulose acetate-butyrate.

37. The method of claim 36 wherein the polyoxyethylene polymer is grafted through a diisocyanate link to the cellulose acetate-butyrate polymer.

* * * * *